United States Patent
Sørensen et al.

(10) Patent No.: US 12,053,152 B2
(45) Date of Patent: *Aug. 6, 2024

(54) TIP PART FOR A VISION DEVICE

(71) Applicant: Ambu A/S, Ballerup (DK)

(72) Inventors: Morten Sørensen, Ballerup (DK); Thomas Bachgaard Jensen, Copenhagen V (DK); Morten Jacobsen, Hørsholm (DK)

(73) Assignee: AMBU A/S, Ballerup (DK)

( * ) Notice: Subject to any disclaimer, the term of this patent is extended or adjusted under 35 U.S.C. 154(b) by 396 days.

This patent is subject to a terminal disclaimer.

(21) Appl. No.: 16/351,632

(22) Filed: Mar. 13, 2019

(65) Prior Publication Data

US 2019/0282077 A1    Sep. 19, 2019

(30) Foreign Application Priority Data

Mar. 14, 2018 (EP) .................................. 18161746
Mar. 14, 2018 (EP) .................................. 18161752

(Continued)

(51) Int. Cl.
*A61B 1/00* (2006.01)
*A61B 1/06* (2006.01)
(Continued)

(52) U.S. Cl.
CPC ...... *A61B 1/00096* (2013.01); *A61B 1/00103* (2013.01); *A61B 1/0011* (2013.01);
(Continued)

(58) Field of Classification Search
CPC ....... B29L 2031/753; B29L 2031/7542; B29L 2031/7543; B29L 2031/7548;
(Continued)

(56) References Cited

U.S. PATENT DOCUMENTS 4,496,211 A * 1/1985 Daniel .................. G02B 6/262
385/147
4,533,243 A * 8/1985 Zhukov ................. G01J 5/041
356/44
(Continued)

FOREIGN PATENT DOCUMENTS

DE    19815598 A1    10/1999
DE    10010931 A1    9/2001
(Continued)

OTHER PUBLICATIONS

Non-Final Rejection Mailed on Apr. 14, 2021 for U.S. Appl. No. 17/149,686.
(Continued)

*Primary Examiner* — Aaron B Fairchild
*Assistant Examiner* — Stephen Floyd London
(74) *Attorney, Agent, or Firm* — Faegre Drinker Biddle & Reath LLP (57) ABSTRACT

A tip part for an insertable vision device, and an insertable vision device including the tip part. The tip part includes a housing accommodating an electronic vision receptor and adapted to extend from a distal end of an insertable elongate portion of the insertable vision device, and a light guide positioned within the housing, the light guide having a predetermined length in a longitudinal direction between a light reception end and a light emission end, the light reception end configured to receive light emanated from a light source and the light emission end configured to emit the light. The light guide includes, along at least a portion of the predetermined length, an expanding sector or a narrowing sector.

20 Claims, 4 Drawing Sheets

(30) Foreign Application Priority Data

| Mar. 14, 2018 | (EP) | 18161762 |
|---|---|---|
| Mar. 11, 2019 | (EP) | 19161893 |
| Mar. 11, 2019 | (EP) | 19161898 |
| Mar. 11, 2019 | (EP) | 19161907 |

(51) Int. Cl.
  *A61B 1/07* (2006.01)
  *B29C 45/16* (2006.01)
  *B29L 31/00* (2006.01)
  *G02B 23/24* (2006.01)

(52) U.S. Cl.
  CPC ........ *A61B 1/00137* (2013.01); *A61B 1/0684* (2013.01); *A61B 1/07* (2013.01); *B29C 45/16* (2013.01); *B29K 2995/0026* (2013.01); *B29L 2031/753* (2013.01); *G02B 23/2476* (2013.01)

(58) Field of Classification Search
  CPC . A61B 1/0008; A61B 1/00096; A61B 1/0011; A61B 1/00167; A61B 1/05; A61B 1/051; A61B 1/053; A61B 1/0676; A61B 1/0694; A61B 1/07; A61B 1/00135; G02B 23/26; G02B 6/0028; G02B 6/0046; G02B 6/0048; G02B 6/0095; G02B 23/2469
  See application file for complete search history.

(56) References Cited

U.S. PATENT DOCUMENTS

| | | | |
|---|---|---|---|
| 4,805,596 A | 2/1989 | Hatori | |
| 4,923,276 A * | 5/1990 | Wells | G02B 6/06 244/3.16 |
| 4,941,457 A * | 7/1990 | Hasegawa | A61B 1/00165 356/241.4 |
| 5,193,525 A | 3/1993 | Silverstein et al. | |
| 5,193,526 A | 3/1993 | Daikuzono | |
| 5,325,845 A | 7/1994 | Adair | |
| 5,408,572 A * | 4/1995 | Kriege | G02B 5/00 385/43 |
| 5,718,663 A | 2/1998 | Wulfsberg | |
| 5,873,877 A * | 2/1999 | McGaffigan | A61B 1/00179 606/41 |
| 5,928,136 A | 7/1999 | Barry | |
| 5,993,378 A | 11/1999 | Lemelson | |
| 7,662,094 B2 | 2/2010 | Iddan | |
| 8,414,480 B2 | 4/2013 | Kendale et al. | |
| 8,485,966 B2 | 7/2013 | Robertson | |
| 8,790,250 B2 | 7/2014 | Petersen et al. | |
| 8,948,560 B1 * | 2/2015 | Wach | A61B 1/07 385/125 |
| 9,220,400 B2 | 12/2015 | Petersen | |
| 9,521,942 B2 | 12/2016 | Robertson | |
| 9,622,649 B2 | 4/2017 | Lin | |
| 9,633,649 B2 | 4/2017 | Lin | |
| 9,854,962 B2 | 1/2018 | McGrail et al. | |
| 10,245,402 B2 | 4/2019 | Daher et al. | |
| 10,321,804 B2 | 6/2019 | Jacobsen et al. | |
| 10,835,103 B2 | 11/2020 | Tamura et al. | |
| 11,291,352 B2 | 4/2022 | Sørensen et al. | |
| 11,779,197 B2 | 10/2023 | Sørensen et al. | |
| 2003/0227547 A1 | 12/2003 | Iddan | |
| 2004/0064018 A1* | 4/2004 | Dunki-Jacobs | A61B 1/07 600/178 |
| 2004/0199052 A1 | 10/2004 | Banik et al. | |
| 2004/0242963 A1 | 12/2004 | Matsumoto et al. | |
| 2005/0046807 A1* | 3/2005 | Hanano | G02B 6/4298 353/98 |
| 2005/0049462 A1 | 3/2005 | Kanazawa | |
| 2005/0203341 A1 | 9/2005 | Welker et al. | |
| 2007/0249907 A1 | 10/2007 | Boulais et al. | |
| 2008/0242935 A1 | 10/2008 | Inoue | |
| 2009/0054728 A1 | 2/2009 | Trusty | |
| 2009/0177040 A1 | 7/2009 | Lyons et al. | |
| 2009/0209819 A1 | 8/2009 | Kitagawa et al. | |
| 2009/0292168 A1* | 11/2009 | Farr | A61B 1/00186 600/109 |
| 2010/0217082 A1 | 8/2010 | Ito et al. | |
| 2010/0286475 A1 | 11/2010 | Robertson | |
| 2011/0118549 A1 | 5/2011 | Han | |
| 2012/0041268 A1* | 2/2012 | Grey | A61B 1/0623 600/199 |
| 2012/0323078 A1 | 12/2012 | Kikumori et al. | |
| 2013/0175720 A1 | 7/2013 | Otsuka et al. | |
| 2013/0271588 A1 | 10/2013 | Kirma et al. | |
| 2013/0329433 A1* | 12/2013 | Lin | G02B 6/4296 362/294 |
| 2014/0081085 A1 | 3/2014 | Takato et al. | |
| 2014/0328047 A1* | 11/2014 | Kamee | F21V 9/08 362/84 |
| 2015/0036146 A1* | 2/2015 | Staloff | A61B 5/0066 356/479 |
| 2015/0335227 A1 | 11/2015 | Jacobsen et al. | |
| 2016/0106306 A1 | 4/2016 | Furuta | |
| 2017/0245734 A1* | 8/2017 | Kaneko | A61B 1/307 |
| 2018/0084981 A1* | 3/2018 | Wang | A61B 1/00172 |
| 2018/0140172 A1* | 5/2018 | Hu | A61B 1/0669 |
| 2018/0310890 A1 | 11/2018 | Li | |
| 2019/0033506 A1* | 1/2019 | Weber | A61B 1/00167 |
| 2019/0175007 A1 | 6/2019 | Sørensen et al. | |
| 2019/0227298 A1* | 7/2019 | Elmaanaoui | A61B 1/00177 |
| 2019/0282070 A1 | 9/2019 | Vilhelmsen et al. | |
| 2019/0313891 A1* | 10/2019 | Oka | A61B 1/0623 |
| 2019/0350442 A1* | 11/2019 | Giessen | A61B 1/00188 |
| 2019/0374092 A1* | 12/2019 | Wu | A61B 1/00096 |
| 2020/0110256 A1* | 4/2020 | Altshuler | G02B 23/02 |
| 2020/0174174 A1* | 6/2020 | Honda | A61B 1/00096 |
| 2021/0127955 A1 | 5/2021 | Sorensen et al. | |
| 2022/0133133 A1 | 5/2022 | Vilhelmsen et al. | |

FOREIGN PATENT DOCUMENTS

| | | |
|---|---|---|
| DE | 102015103214 A1 * | 9/2016 |
| DE | 102018110620 A1 | 11/2019 |
| JP | 3764512 B2 | 4/2006 |
| JP | 2009-125528 A | 6/2009 |
| JP | 2018-015250 A | 2/2018 |
| WO | WO 2005/023099 A1 | 3/2005 |
| WO | 2009/100368 A1 | 8/2009 |
| WO | 2010/066790 A1 | 6/2010 |
| WO | 2014/106511 A1 | 7/2014 |
| WO | 2017/104048 A1 | 6/2017 |
| WO | 2018/059643 A1 | 4/2018 |

OTHER PUBLICATIONS

OEE—Intention to Grant under Rule 71(3), dated Dec. 23, 2020 in related EP Application No. 19161907.1, including specification, claims, and drawings.
Extended Search Report dated Apr. 2, 2019 in related EP Application No. 19161893.3.
Extended Search Report dated Apr. 2, 2019 in related EP Application No. 19161907.1.
Extended Search Report dated Apr. 2, 2019 in related EP Application No. 19161898.2.
Extended search report dated Oct. 15, 2018 in related EP Application No. 18161752.3.
Extended search report dated Oct. 15, 2018 in related EP Application No. 18161762.2.
Extended search report dated Oct. 26, 2018 in related EP Application No. 18161746.5.
Search report in European application No. 19 161 893.3 mailed Jul. 5, 2019, 13 pgs.
Extended European search report issued in European patent application No. 23198550.8, dated Nov. 28, 2023.

(56) References Cited

OTHER PUBLICATIONS

Extended European search report issued in European patent application No. 23205565.7, dated Jan. 23, 2024; 5 pages.

* cited by examiner

TIP PART FOR A VISION DEVICE

CROSS-REFERENCE TO RELATED APPLICATIONS

This patent application claims priority to and the benefit of European Patent Applications Nos. 18161752 and 18161762, entitled A TIP PART FOR A VISION DEVICE, filed on Mar. 14, 2018, of European Patent Application No. 18161746, entitled METHOD FOR MANUFACTURING A TIP HOUSING, filed on Mar. 14, 2018, of European Patent Application No. 19161898, entitled A TIP PART FOR A VISION DEVICE, filed on Mar. 11, 2019, of European Patent Application No. 19161907, entitled A TIP PART FOR AN INSERTABLE VISION DEVICE, filed on Mar. 11, 2019, and of European Patent Application No. 19161893, entitled METHOD FOR MANUFACTURING A POT-SHAPED TIP HOUSING, filed on Mar. 11, 2019, respectively, all of which are incorporated by reference herein in their entirety.

TECHNICAL FIELD

The present disclosure relates to insertable vision devices such as but not limited to endotracheal tubes and endoscopes, more specifically to a tip part of such an insertable vision device and an insertable vision device.

BACKGROUND

Insertable vision devices such as endoscopes are well known for visually inspecting inaccessible places such as body cavities, e.g. human body cavities. Typically, the endoscope comprises an elongated insertion tube with a handle at the proximal end as seen from the operator and visual inspections means, such as a built in camera, at the distal end of the elongated insertion tube. Electrical wiring for the electronic vision receptor, e.g. the chip of a camera, and other electronics, such as Light Emitting Diode (LED) lighting, accommodated in the tip part at the distal end run along the inside of the elongated insertion tube from the handle to the tip part. Instead of using cameras, endoscopes may also be fiber-optic, in which case the optical fibers run along inside of the elongated insertion tube to the tip part.

In order to be able to maneuver the endoscope inside the body cavity, the distal end of the endoscope may comprise a bending section with increased flexibility, e.g. a number of articulated segments of which the tip part forms the distalmost segment. This is typically done by tensioning or slacking pull wires also running along the inside of the elongated insertion tube from the tip part through the remainder of articulated segments to a control mechanism of the handle. Furthermore, a working channel may run along the inside of the insertion tube from the handle to the tip part, allowing liquid to be removed from the body cavity or allowing the insertion of surgical instruments or the like into the body cavity.

As the name indicates, endoscopes, are used for seeing inside things, such as lungs or other body cavities of a patient. Modern endoscopes are therefore typically equipped with a least one camera or similar image capturing device serving as an electronic vision receptor at the distal tip of the endoscope. Provided that sufficient light is present, this allows the operator to see where the endoscope is steered and to set the target of interest once the tip has been advanced thereto. This therefore normally requires illumination of the area in front of the distal tip of the endoscope, in particular the field of vision of the camera(s). One known way of achieving such illumination is to provide the above mentioned LED lighting using one or more LEDs in the tip of the endoscope, as e.g. mentioned in WO2014/106511 disclosing a disposable endoscope. The light distribution in the emitted light from a light source such as an optical fiber or an LED is, however, not optimal as regards the field of vision of a vision receptor such as an image sensor, a video camera or an optical fiber. In particular, an LED may spread the emitted light over a wide angle. If light is emitted at an angle so wide that it illuminates objects outside the field of vision of the vision receptor, it is largely wasted. Also, in many body cavities, in particular tubular ones, objects in the periphery of the field of vision will often be closer than those in the center. Consequently, they will be stronger illuminated than those in the center, which in turn leads to overexposure of the image at the periphery and underexposure in the center where the object of interest is often likely to be.

When the insertion tube of the endoscope is intended to be inserted into a human body cavity, the insertion tube furthermore needs to be sealed in a watertight manner. This is in particular the case for the distal tip part because it accommodates the camera, LED(s) and other delicate electronics, prone to malfunction or destruction if exposed to humidity.

One known way of sealing the tip part of an endoscope is disclosed in WO2010/066790. In this document a transparent monolithic housing is formed around the electronics and working channel by placing the electronics and the tube forming the working channel in a mold of transparent material, such as silicone. A transparent UV curable resin is then inserted from the bottom of the mold to avoid bubbles to form in the transparent resin. Because the resin rises slowly from the bottom, the air is slowly expelled from top of the mold, without any risk of air bubbles being trapped in the mold. The resin is then cured using UV irradiation through the transparent mold to form the monolithic housing. However, forming a monolithic housing in this way has some drawbacks. One is that it is a somewhat slow process. Another is that it can be difficult to position and maintain the components precisely in position during the insertion of the resin. Thus the camera or LEDs may be off-set sideways or a thin transparent layer may inadvertently be created in front of the camera and/or LEDs, thereby reducing the imaging qualities of the tip part.

It is the object of the present disclosure to provide a tip part of an insertable vision device which overcomes at least some of the above problems.

SUMMARY

A tip part for an insertable vision device, and insertable vision devices comprising the tip part, are provided herein. The tip part may include an expanding sector, and/or a narrowing sector, and perhaps a sector of constant cross-section. The expanding sector reduces instances of light rays refracting out of the side surfaces of a light guide, increasing the light efficiency of the tip portion and thus enabling reductions in electrical energy and the need to dissipate heat resulting from the use of the electrical energy for illumination purposes. The expanding sector focuses or collimates the light beam to improve the quality of video images captured by the insertable vision device at the proximal end of the light guide. The narrowing sector disperses the light beam at the distal end of the light guide. The tip part may have a housing, at least a portion of said housing made in one-piece with the light guide.

In one embodiment, a tip part for an insertable vision device is provided, the tip part comprising an electronic vision receptor; a housing accommodating the electronic vision receptor and adapted to extend from a distal end of an insertable elongate portion of the insertable vision device; and a light guide made of a transparent material and positioned within the housing, the light guide having a predetermined length in a longitudinal direction between a light reception end and a light emission end of the light guide, the light reception end configured to receive light emanated from a light source and the light emission end configured to emit the light, wherein the light guide is adapted to reshape an incoming light beam and comprises, along at least a portion of the predetermined length, an expanding sector and/or a narrowing sector having cross-sectional areas, perpendicular to a longitudinal axis of the light guide, that increase or decrease, respectively, in the direction from the light reception end toward the light emission end.

In another embodiment, an insertable vision device is provided, the insertable vision device comprising a tip part, the tip part comprising: an electronic vision receptor; a housing accommodating the electronic vision receptor and adapted to extend from a distal end of an insertable elongate portion of the insertable vision device; and a light guide made of a transparent material and positioned within the housing, the light guide having a predetermined length in a longitudinal direction between a light reception end and a light emission end of the light guide, the light reception end configured to receive light emanated from a light source and the light emission end configured to emit the light, wherein the light guide comprises, along at least a portion of the predetermined length, an expanding sector and/or a narrowing sector having cross-sectional areas, perpendicular to a longitudinal axis of the light guide, that increase or decrease, respectively, in the direction from the light reception end toward the light emission end.

In a further embodiment, a tip part for an insertable vision device is provided, which is adapted to reshape an incoming light beam, the tip part comprising: an electronic vision receptor; a housing adapted to extend from a distal end of an insertable elongate portion of the insertable vision device; and at least one light guide made of a transparent material and positioned within the housing, the at least one light guide having a predetermined length in a longitudinal direction between a light reception end and a light emission end of the light guide, the light reception end configured to receive light emanated from a light source and the light emission end configured to emit the light, wherein the housing comprises a first housing part and a second housing part, the first housing part molded, together with the light guide, from a first transparent material in one-piece, and the second housing part accommodating the insertable vision device.

In a yet further embodiment, an insertable vision device is provided, the insertable vision device comprising a tip part, the tip part comprising: an electronic vision receptor; a housing adapted to extend from a distal end of an insertable elongate portion of the insertable vision device; and at least one light guide made of a transparent material and positioned within the housing, the at least one light guide having a predetermined length in a longitudinal direction between a light reception end and a light emission end of the light guide, the light reception end configured to receive light emanated from a light source and the light emission end configured to emit the light, wherein the housing comprises a first housing part and a second housing part, the first housing part molded, together with the light guide, from a first transparent material in one-piece, and the second housing part accommodating the insertable vision device.

Furthermore, according to a first aspect of the disclosure, at least one object of the invention is achieved by a tip part for an insertable vision device, said tip part comprising a housing adapted for accommodating an electronic vision receptor, at least one light guide of a transparent material having a predetermined length in a longitudinal direction between at least one first light reception end adapted for receiving light from a light source and at least one second light emission end adapted to emit light. In this way it becomes possible to control the light emission characteristics from the tip of the endoscope, in particular so as to obtain a desired light distribution profile, matching e.g. the field of vision of the vision receptor, while at the same time ensuring a good coupling of light from the light source into the light guide.

In one variation, along the predetermined length the light guide comprises an expanding sector in which the light guide has a varying cross-sectional area. In one example, in said expanding sector the cross-sectional area is increasing in the direction from the at least one light reception end towards the at least one light emission end. The cross-sectional area may increase continuously, e.g. monotonously, in which the rate of increase is constant, or at different rate of increase.

In another variation, the housing comprises a first housing part, made from a transparent material, and a second housing part. The light guide in the present variation is provided in a one-piece construction with the first housing part. In one example, the first housing part includes a window at its distal end, through which the camera captures images of the field of view. The light guide is disposed proximally of the window. By integrating the light guide in the housing, it is possible to provide a sealed front end of the tip part while providing a well defined exit viewing angle for the light from the light source, in a device that is economical to manufacture. Also, the transfer of light from a light guide material to a window material is avoided.

In another variation, the light guide comprises, along the predetermined length, a narrowing sector, distal of the expanding sector, in which the light guide has a varying cross-sectional area where the varying cross-sectional area is decreasing in the direction from the at least one light reception end towards the at least one light emission end. The cross-sectional area may decrease continuously, monotonously, or at different rates. It has been found that by introducing such a narrowing sector, in particular at or around the essentially plane light emission surface of the end face, a good light distribution in the field of vision in front of the electronic vision receptor may be obtained.

According to another embodiment, the predetermined length further comprises one or more sectors of constant cross-sectional area. This is advantageous when the predetermined length exceeds the necessary length of the expanding and/or narrowing sectors. In this way angles may still be chosen of the expanding and/or narrowing sectors which ensure total internal reflection in these sectors.

Thus, according to a further embodiment, said increasing and/or decreasing cross-sectional area changes in such a way along the length of said at least one sector that total internal reflection of light from the light source is provided.

According to another embodiment of the present invention, said at least one sector with the increasing cross-sectional area comprises a truncated pyramid. Having a linearly expanding cross-section provides good control over the total internal reflection properties of the light guide, in turn aiding in providing the above mentioned desired light distribution profile.

According to another embodiment, the cross-sectional area has, along at least a part of the predetermined length, the shape of a rectangle. A rectangular shape is preferable because the vision receptor will normally comprise a rectangular field of vision. By also having a cross sectional shape of the light guide, the desired light distribution profile may be made to match at least partially the field of vision of the vision receptor. Thus, less light is wasted.

According to another embodiment, the rectangle has rounded corners. Thereby, disturbances and deviations from the optimally desired light distribution profile may be minimized.

According to a further embodiment, at least the sector with monotonously increasing cross-sectional area of said light guide is surrounded by air. Having air around the light guide, and in particular around the sector with monotonously increasing cross-sectional area, provides good total internal reflection in the light guide and accordingly low light losses.

According to an alternative embodiment, however, at least a part of the light guide is cladded with a cladding. Providing a cladding gives good control over the total internal reflection, and secures that the desired properties are not ruined by ingress of pollutants, e.g. sealing material or glue.

According to another embodiment, the light reception end is adapted to engage an LED. Adapting the light reception end to engage the LED, e.g. by matching surface areas, ensures good light transmission properties across the interface between the LED and the light guide, e.g. avoiding reflections. Furthermore, when the light reception end is so adapted that no glue or the like is necessary any deterioration of phosphorescent material on the LED that could be caused by the glue is avoided.

According to a further embodiment, the light reception end is adapted to engage a light fiber. Adapting the right reception end to engage the light fiber, e.g. by providing the plane surface in the bottom of a bore, ensures good light transmission properties across the interface between the light fiber and the light guide, e.g. avoiding reflections. Furthermore, when the light reception end is so adapted that no glue or the like is necessary any undesired reflections that could be caused by the glue are avoided.

According to yet another embodiment the essentially plane surface of the end face is perpendicular to the longitudinal direction. This further improves the control of the light and the good coupling thereof into the light guide.

According to yet another embodiment, the transparent material comprises polycarbonate. Polycarbonate is advantageous in that it is has good optical properties, is easy to mold, and has low material costs.

According of yet a further embodiment, the light guide forms an integral part of the housing. By integrating the light guide in the housing, it becomes possible to provide a sealed front end of the tip part.

According to a second aspect of the disclosure, an endoscope with a tip as described in any of the embodiments described in the present specification is provided.

According to a second aspect, at least an object of the present invention is achieved by a tip part for an insertable vision device, such as an endoscope, said tip part comprising a housing adapted for accommodating an electronic vision receptor, at least one light guide of a transparent material configured to provide total internal reflection and having a predetermined length between at least one first light reception end adapted for receiving light from a light source and at least one second light emission end adapted to emit light, wherein the housing comprises a first transparent housing part and a second housing part, moulded integrally from a first transparent material and a second material, respectively, and wherein the light guide is provided in one piece with said first housing part from said first transparent material so as to form an integral part of the housing.

By integrating the light guide in the housing, it becomes possible to provide a sealed front end of the tip part and at the same time provide a well-defined exit viewing angle for the light from the light source. A person skilled in the art will appreciate that any one or more of the above aspects of the disclosure and embodiments thereof may be combined with any one or more of the other aspects of the disclosure and embodiments thereof.

BRIEF DESCRIPTION OF THE DRAWINGS

The invention will now be described in greater detail based on non-limiting exemplary embodiments and with reference to the drawings, on which.

DETAILED DESCRIPTION

Figure 1:
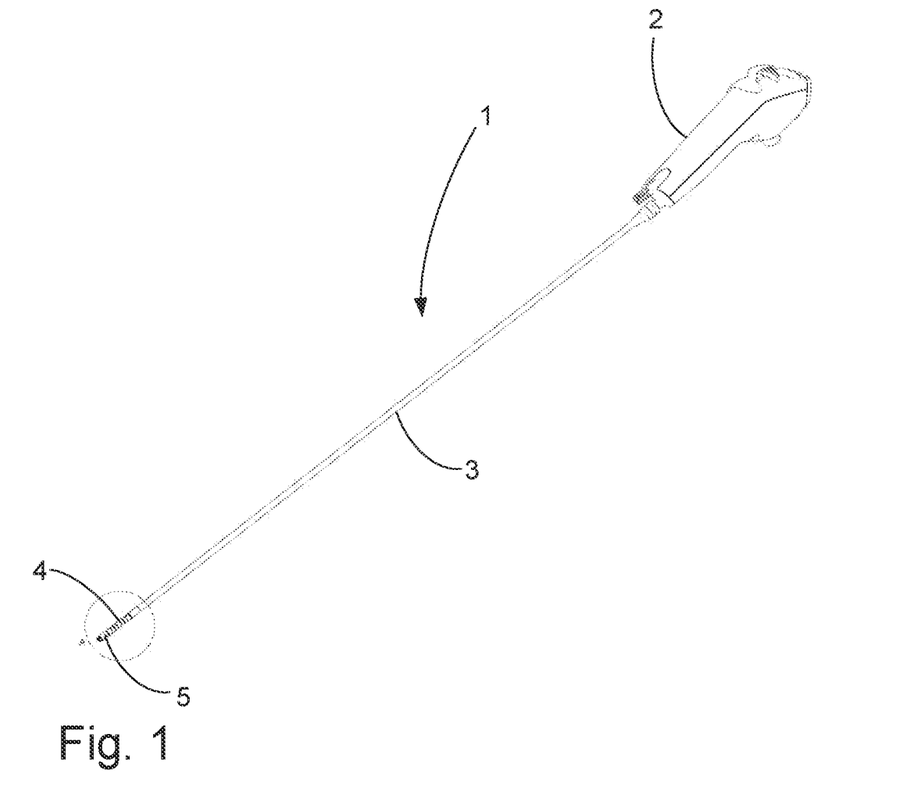
FIG. 1 shows an endoscope according to one embodiment of the present disclosure.

Turning first to FIG. 1, an endoscope 1 comprises a handle 2 at the proximal end, an insertion tube 3 extending towards the distal end where it comprises an articulated bending section 4, which as the most distal segment is connected to a distal tip part 5 via a support member 20 including a proximal end, a distal end, and a plurality of circumferential slots 21 in the proximal end. The proximal end is positioned in the most distal segment of the bending section 4 and the distal end is positioned in a housing of the distal tip part 5 (best seen in FIGS. 4, 5 and 5A). Though omitted for illustration purposes the articulated bending section 4 will normally be covered by a suitable sleeve, connected at least at its own distal end to the distal tip part 5, e.g. by means of an adhesive. This as such is conventional and e.g. known from the aforementioned WO2014/106511. The endoscope 1 is intended as a medical vision device, and is therefore conceived as a disposable endoscope to be thrown away after use in order to avoid cleaning and sterilisation issues. Low manufacturing costs is therefore an important issue.

Figure 2:
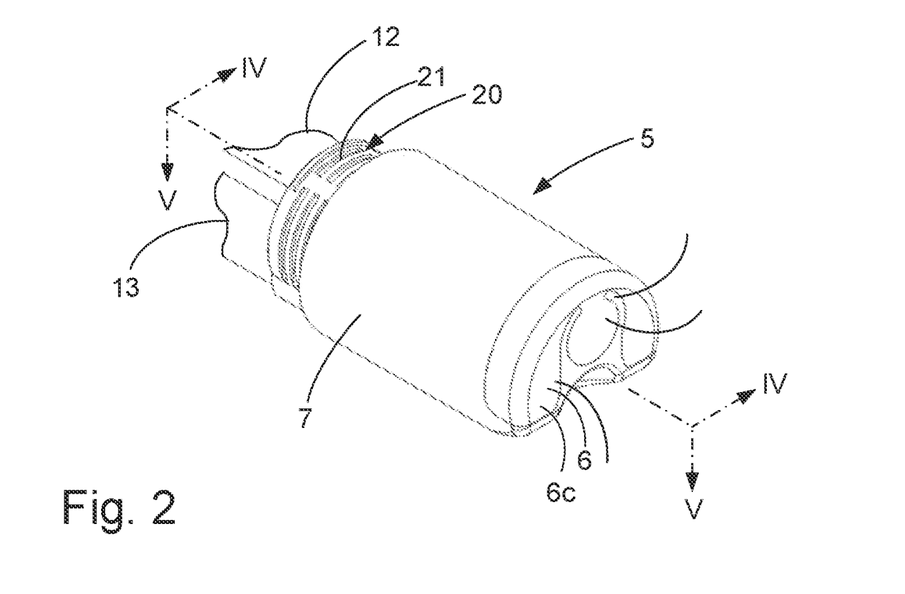
FIG. 2 shows an isometric view of tip part for an endoscope in accordance with an embodiment of the present disclosure.
Figure 3:
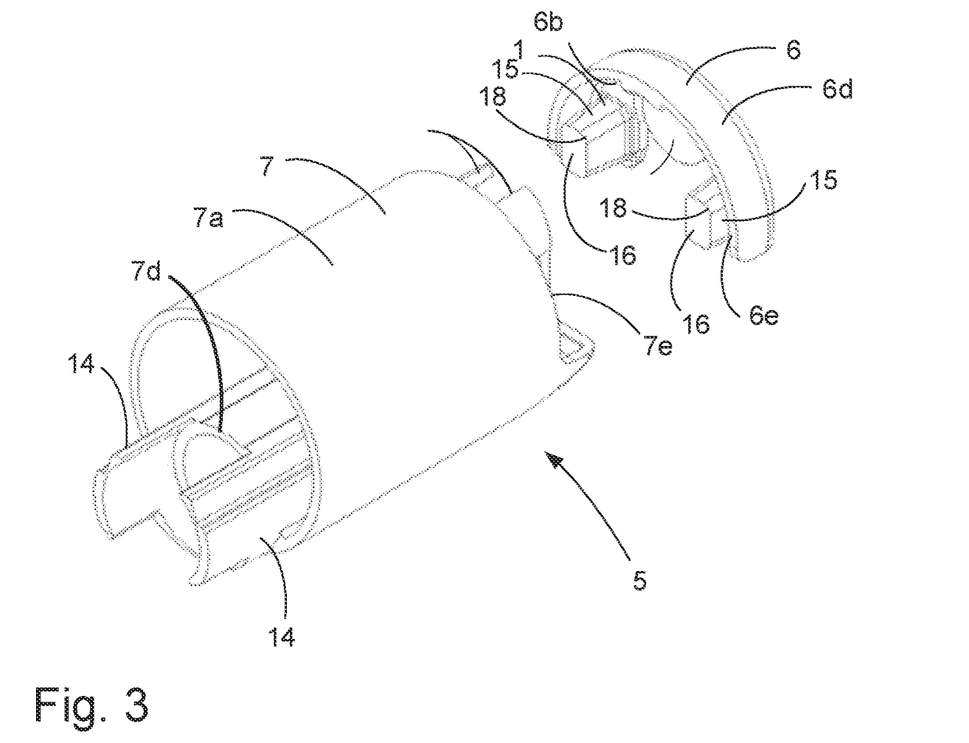
FIG. 3 shows an exploded view of a housing of the tip part of FIG. 1, illustrating light guides in accord with an embodiment of the disclosure.

As best seen in FIGS. 2 and 3, the distal tip part 5 comprises a housing with two housing parts. A first, or distal, housing part 6 made of a suitable transparent material, and a second, or proximal, housing part 7 optimized for other properties such as opacity, softness, elasticity, and/or good adhesive bonding. Though shown as two parts in the exploded view of FIG. 3, the housing need not be assembled from two parts but could be manufactured as a single item of a single transparent material or as a single item of two materials fused or bonded together in the molding process. In that respect it should be noted that this could be done in a two component moulding in which one of the respective first and second housing parts (6, 7) is first moulded as one single piece in a first mould cavity. That housing part is then transferred to a second moulding cavity in which the other housing part (7, 6) is likewise moulded as one single piece. The two integrally formed single pieces will then fuse to an overall integral housing during the second moulding. As seen in FIG. 3 and described with reference to FIG. 5, housing part 6 comprises a window 6a having a distal surface 6c and a proximal surface 6b. A light guide 15 comprises a light emission end 17 opposite a light reception end 16. Light guide 15 extends proximally from proximal, or internal, surface 6b such that light emission end 17 is proximal of proximal surface 6b of window 6a. Housing part 6 also comprises an arcuate wall 6d that is connected to window 6a and extends proximally from distal surface 6c. As seein in FIG. 6, LEDs 9 are longitudinally aligned with light guide 15 such that light emitted by LEDs 9 pass through light guide 15 from light reception end 16 through light emission end 17 and distal surface 6c. Window 6a comprises a viewing part 6f, disposed beween two arcuate walls 7f of the second housing part, that extend proximally from a plane encompassing distal surface 6c, and a light emmission part 6g disposed laterally from the two arcuate walls 7f. A portion of the distal surface 6c encompasses a distal surface of the light emission art 6g, referred to as a light emission surface.

Figure 4:
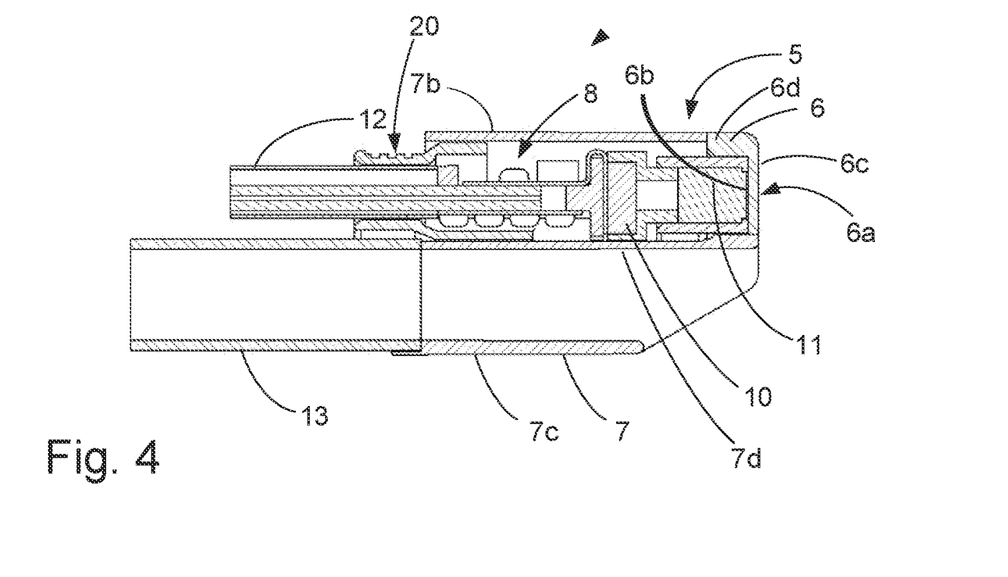
FIG. 4 shows a cross-section of the tip part taken along the line IV-IV in FIG. 2 together with parts of attached tubes.

As best seen in FIG. 4 an electronics module 8 is accommodated in the distal tip part. In the illustrated embodiment the electronics module comprises a light source in the form of a pair of LEDs 9 and a vision receptor such as a video camera 10 or an imaging chip. Possibly with an additional lens assembly 11 arranged in front of the video camera 10 or imaging chip.

Electrical wiring to the electronics module 8 and/or optical fibers for illumination or image capture, if used instead of LEDs and video camera, are led into the housing via a conduit 12 and sealed using a suitable sealing material (not shown). For the purposes of illustration, however, reference is made only to LEDs 9 and video cameras 10. It should also be noted a distinction between optical fibers and light guides. Optical fibers in this context are to be understood as highly elongated and flexible, where the length is several orders of magnitude larger than the diameter, providing the fibers with a high degree for flexibility to allow them to conduct luminous flux to a desired place. Light guides are to be understood as much shorter, preferably rigid items adapted to guide and distribute light in a desired manner. Furthermore, while optical fibers are used to transport light, as used herein light guides are primarily used to reshape the incoming light beam.

Also connected to the housing and sealed is a tube 13 forming part of the working channel of the endoscope 1. In the illustrated embodiment, the tube 13 is connected via a pair of protrusions 14 between which the tube 13 is held, possibly with the aid of an adhesive. Second housing part 7 comprises a cylindrical wall 7a having opposing sides 7b, 7c on opposite sides of a longitudinal axis thereof, and an intermediate wall 7d extending within cylindrical wall 7b between opposing sides 7b, 7c. Cylindrical wall 7a extends proximally from arcuate wall 6d and has a distal surface 7e sized and shaped to fuse with a corresponding proximal surface 6e of arcuate wall 6d.

Figure 5:
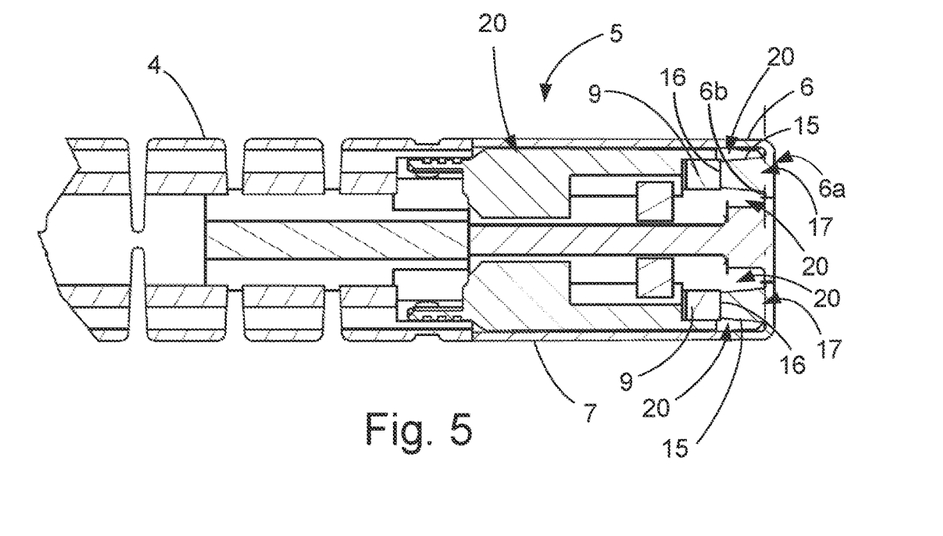
FIGS. 5 and 5A show a cross-section of the tip part taken along the line V-V in FIG. 2 together with parts of a bending section, FIGS. 6, 7 and 8 schematically show different embodiments of the light guide according to embodiments of the disclosure.
Figure 5A:
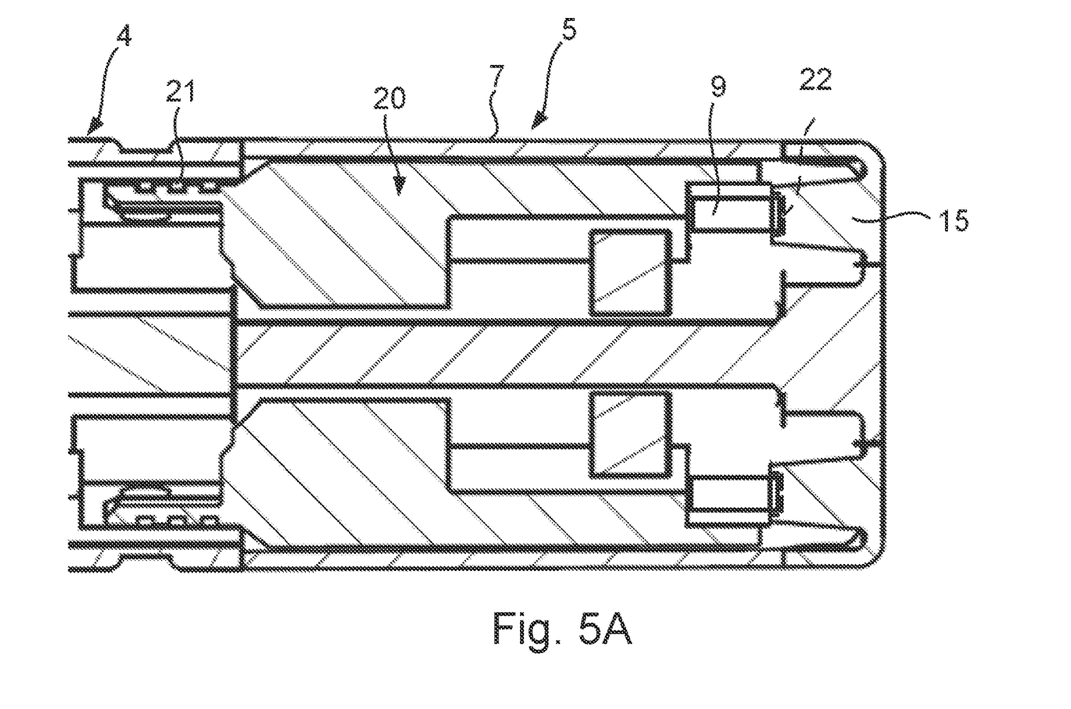
Figure 6:
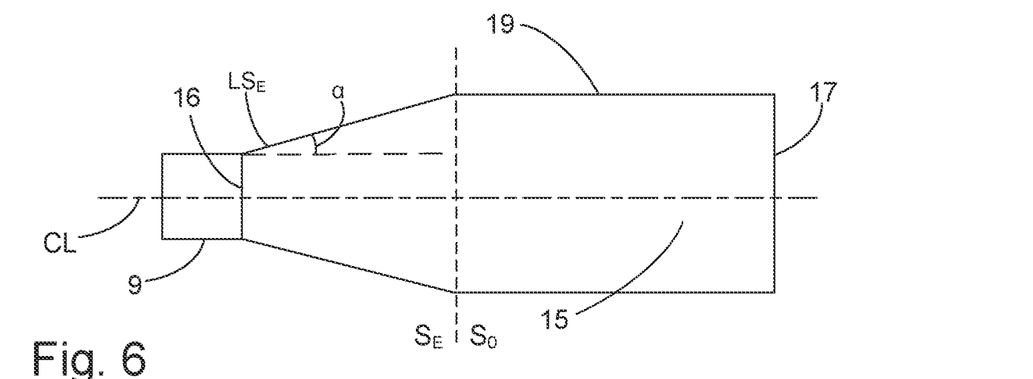
Figure 7:
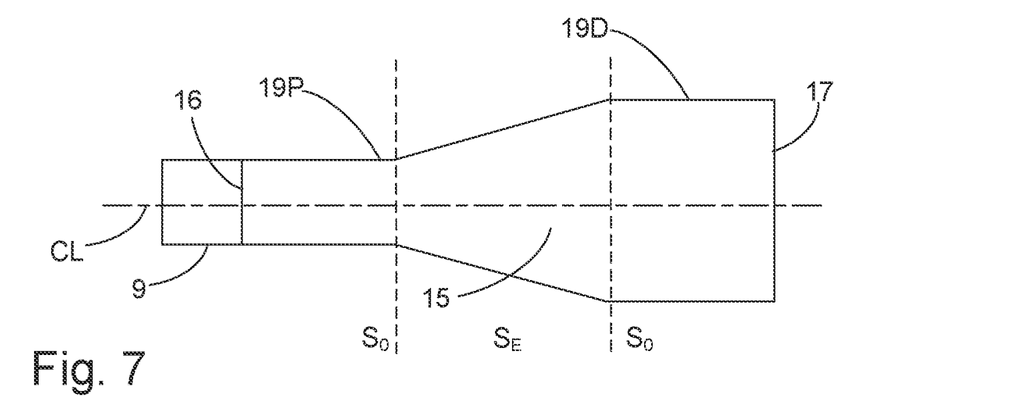
Figure 8:
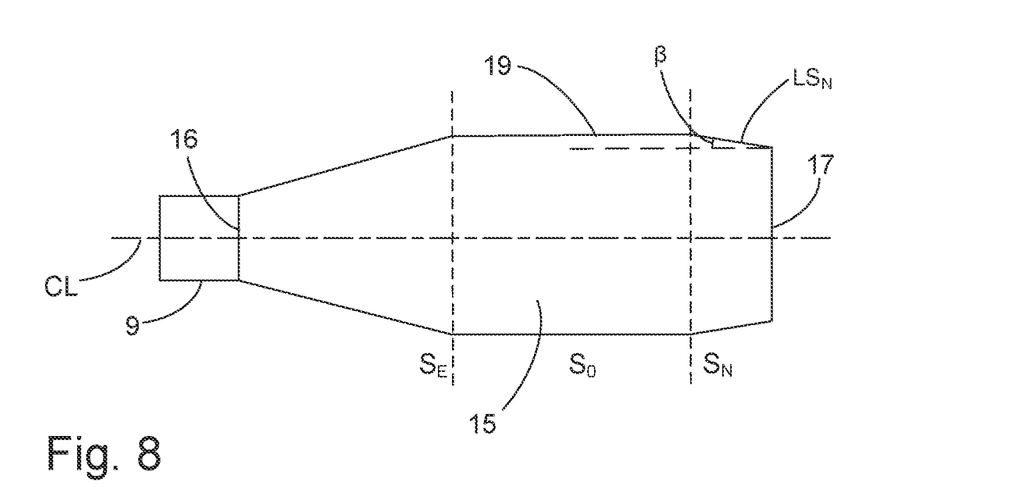

To achieve a desired illumination characteristics or light distribution profile from the light source, i.e. the pair of LEDs 9, the LEDs are located in a retracted manner within the housing (e.g. spaced apart from an internal surface of a viewing window of the housing), and at least one light guide 15 is associated to the LEDs. At the proximal end, the light guide 15 thus comprises a first light receiving end 16 adapted to receive light from the LED, e.g. by having a highly plane surface matching that of the LED in planarity and preferably also in area, e.g. as abutting surface for the LED 9 as illustrated in FIG. 5, or a bore in which the LED is inserted, in particular a bore in the form of a blind hole 22 with a planar bottom, as shown in FIG. 5A, which except for showing the blind hole 22 is an expanded sectional view of FIG. 5. At the distal end, the light guide comprises a second light emission end 17 adapted to emit the light received from the LED 9. In one preferred embodiment, the light guide forms an integral part of the housing as can best be seen from FIGS. 3 and 5. That is to say, the light guide 15 is molded in one single piece integrally with the transparent housing part 6. The transparent housing part 6 and the second housing part 7 may be formed directly as a single piece by two component molding, or they may be joined to an integral housing by gluing welding or the like in a separate step. Alternatively, to the integration into the housing, the light guide(s) may be made as separate elements, as indicated in FIGS. 6, 7 and 8, interposed between the LEDs and the transparent housing part 6.

The light guides 15 are configured to utilize the principle of total internal reflection (TIR) to provide the desired illumination characteristics or light distribution profile from the light source. TIR is based on the characteristics of the materials, which define a critical angle. The critical angle is measured from a plane perpendicular to a transition surface between two mediums, one being the material of the light guide and the other being the material or volume surrounding it. If the angle of incidence of light rays emitted by a light source into the light guide is larger than the critical angle, meaning that rays are closer to being parallel to the transition surface, the rays refracted at the transition surface will not emerge from the medium in which they are transmitted but will be reflected back into the medium. The geometry of the light guides 15 are configured, together with the choice of light source and materials, to substantially reduce the likelihood of a light ray impinging on the transition surface at an angle smaller than the critical angle. The configurations may involve index of refraction of the material, transparency, length, variation of the cross-sectional area, geometry of the cross-section, cladding etc.

Generally, to achieve TIR light has to travel from an optically denser medium (higher refractive index) to an optically less dense medium (lower refractive index). If cladding is used, the cladding has to be optically less dense than the material of the light guide, which is why air works well. Example materials for the light guide include acrylic (poly(methylmethacrylate)(PMMA), polycarbonate, glass, and other polymers. The critical angle is defined by the relationship between the refractive index of the light guide material and the refractive index of the surrounding medium. For example, when surrounded by air, the critical angle for acrylic is 42 degrees, and glass would define a different critical angle.

Since video cameras 10 are generally adapted for capturing a rectangular image it has been realized that using light guides 15 with a generally rectangular cross-section is advantageous. As compared to circular ones, more light can be directed towards the corners. Also, potentially less light will be wasted by not illuminating areas outside the rectangular field of vision of the video camera. This applies even if a pair of LEDs 9 is used, and even if the shape of the rectangular cross-section does not match the aspect ratio of the video camera 10. It has been found, however, that using rectangular cross-sections with rounded corners 18, as can be seen in FIG. 3, is advantageous as it gives better control over the light distribution in the corners of the field of vision of the video camera 10. In particular artefacts produced by multiple reflections in sharp corners are avoided. Preferably, the rectangular cross-section as is present along the entire length of the light guide 15, be it with the rounded corners 18 or not. Though less preferred, the use of other cross-sectional shapes, in particular elliptical or circular, but also polygons with or without rounded corners are not excluded.

To utilize best possibly the total internal reflection, the cross-sectional area of the light guide 15 varies along the predetermined length. As can be seen from FIGS. 6 to 8, the predetermined length comprises a number of sectors, indicated by $S_E$, $S_0$ and $S_N$, indicating sectors with expanding, constant, and narrowing cross-sectional areas, respectively. More specifically it varies in a way where the cross-sectional area in a sector is either constant, monotonously increasing or monotonously decreasing from the at least one light reception end 16 towards the at least one light emission end 17. In FIG. 3 where the area of cross-section monotonously increasing sector increases linearly the sector thus comprises a truncated pyramid. If the cross-section was different, analogous shapes would apply, e.g. a truncated cone for a circular cross-section. It should be emphasized that the monotonous increase need not be linear.

If a sector $S_0$ with a constant area 19 is also used, this sector could be arranged on any side of the sector with the monotonously increasing cross-sectional area, be it proximal as in FIG. 6, distal or both, as in FIG. 7 (shown as 19P and 19D denoting proximal and distal areas 19 of sectors $S_0$). It could also be arranged somewhere in the middle, as indicated in FIG. 8. If total internal reflection is present in all sectors it is of less importance where the monotonously increasing cross-sectional area is located. However, if there is a cladding there is a risk that there is not total internal reflection. It may therefore be preferred that the increase in area starts immediately from the LEDs which changes the angle of incidence of light impinging on the surface, thereby ensuring total internal reflection of more light towards the light emission end. Thus the light from the LEDs get more parallel or collimated and the angle over which the light is emitted becomes narrower and matches the field of vision of the video camera better. If the collimation is narrower than desired, as it would typically be if the light source is the exit aperture of a light fiber, it may be necessary to provide light scattering features at the exit end of the light guide, such as a chamfering of the edges. Thus, as can be seen in FIG. 8, there is a sector $S_N$ towards the light emission end 17, where the cross-sectional area monotonously decreases. Like the increase mentioned above, this decrease is preferably selected to that total internal reflection is ensured.

Other configurations of constant and increasing areas are not excluded. It should also be noted that the truncated pyramids of FIG. 3 may be implemented as separate elements, and conversely the shapes described in conjunction with FIGS. 6, 7 and 8 may be formed integrally with the transparent housing part 6. The use of one or more constant area sectors $S_0$, may allow the predetermined length to be adapted to other structural features such as the length of the lens assembly 11, the location of the LEDs on a circuit board carrying the video camera 10 and other components of the electronics section 8.

To ensure good total internal reflection in order to keep the light within the light guide and/or control the exit angle from the distal end 17 it is preferred to surround at least the sector $S_E$ with increasing cross-sectional area or the sector $S_N$ with decreasing cross-sectional area of the light guide is surrounded by air as illustrated by the cavities 20 in FIG. 5. Alternatively, a cladding, e.g. a glue, with a predetermined index of refraction may be used. A cladding may be advantageous in cases where the components are not arranged in a pre-fabricated housing, but rather molded-in in housing material after assembly, because in such cases it may be difficult to ensure the existence of the air filled cavities 20 around the light guides 15.

As for the transparency and the index of refraction of the transparent material 6 the transparent material 6 may comprise polycarbonate, which has suitable properties and may be injection molded for efficient manufacture. If no cladding is present, i.e. the polycarbonate is surrounded by air, the minimum angle of incidence of light ensuring total internal reflection is 39 degrees. Other transparent materials will result in other minimum angles, as will cladding. The critical angle for glass is 30-42 degrees.

Referring again to FIGS. 5 and 6, the expanding sector $S_E$ has cross-sectional areas, perpendicular to a longitudinal axis, or centerline CL, of the light guide, that increase in the direction from the light reception end 16 toward the light emission end 17. The expanding sector comprises a proximal surface perpendicular to the longitudinal axis and having a proximal cross-sectional area, e.g. light reception end 16, that is smaller than any other of the cross-sectional areas of the expanding sector, a distal cross-sectional area (at the transition between $S_E$ and $S_0$) that is larger than any other of the cross-sectional areas of the expanding sector, and a lateral surface, $LS_E$, extending from the proximal cross-sectional area to the distal cross-sectional area at an alpha angle, a, from the longitudinal axis, ranging between about 1 to 20 degrees, more preferrably between 4 and 16 degrees, and even more preferrably between 6 and 12 degrees. Although shown as a flat surface, lateral surface $LS_E$ could be curved along either axis, thereby the cross-sections would be continuously increasing albeit at different rates. The selection of the light guide medium and the surrounding medium defines the critical angle and the combination of the material and the alpha angle reduces light losses. For example, an LED placed adjacent the light reception end 16 might emanate light rays in various angles, including angles larger than the critical angle. The addition of the expanding sector reduces instances of light rays impinging on the transition surface (e.g. at angle alpha) at incidence angles greater than the critical angle, thereby allowing more of the rays to have the advantage of total internal reflection, thereby increasing the light efficiency of the tip portion and thus enabling reductions in electrical energy and the need to dissipate heat generated by the LEDs. The angle alpha must be selected in relation the desired sizes of the LED, which may depend on desired illumination strength, and the overall cross-section of the tip portion, which may depend on the procedure for which the insertable vision device is designed. In one example, the expanding sector comprises a polymeric material and the expanding sector is geometrically configured such that at least 95%, and more preferably 98%, of the light received at the light reception end is reflected and at most 5%, and more preferably 98%, of the light is refracted.

In the embodiment depicted in FIG. 8, the narrowing sector $S_N$ comprises a proximal cross-sectional area perpendicular to the longitudinal axis (at the transition between $S_O$ and $S_N$) that is larger than any other of the cross-sectional areas of the narrowing sector, a distal cross-sectional area that is smaller than any other of the cross-sectional areas of the narrowing sector (e.g. light emission end 17), and a lateral surface, $LS_N$, extending from the proximal cross-sectional area to the distal cross-sectional area at a beta angle, from the longitudinal axis, smaller than about 14 degrees, more preferrably smaller than about 12 degrees, and even more preferrably smaller than 10 degrees. For an LED light source, the alpha angle may be greater than the beta angle so as to achieve TIR and a suitable beam and field of view. For a narrow beam light source, such as a light fiber, the alpha angle may be smaller than the beta angle. If the light source beam is narrower than the desired emitted beam, the expanding sector may be omitted or may have an alpha angle that is very small, between 0-7 degrees. As shown, the beta angle has an origin distal of the proximal cross-sectional area. As described previously, the narrowing sector focuses the light intensity at the center of the beam, improving the quality of the images obtained with the camera. Of course, the use of a narrowing sector, and the selection of the angle beta, may dependend on the use and size of the expanding sector.

In one example, the light guide is made of polycarbonate, which has a refractive index of 1.586, and there is a glue or cladding as the surrounding medium, which has a refractive index of 1.49. The light source is an LED, which generally has 180 degree beam. In this case, the alpha angle of between 10 degrees and 19.5 degrees will in theory keep all the light rays inside the light guide and will concentrate the wide beam of the LED. Although these angles will give the benefit of having more or all the light rays being kept inside the light guide, there is also a drawback that the exiting light profile may become too narrow to fit the camera field of view. To compensate for this, the beta angle may be adjusted accordingly. For example, if the alpha and beta angles are identical, the light rays will be spread to the same distribution as the incoming light when entering the light guide. If the incoming light is distributed over 180 degrees from the light source, which is usually the case with LEDs, then having the alpha angle equal to the beta angle will result in a 180 degree beam.

If the beta angle is smaller than the alpha angle, the resulting effect of the light guide will be a collimating effect which can be used to optimize the exiting light profile in relation to the camera field of view. For example, if the alpha angle is 10 degrees and the beta angle is 7 degrees with the incoming light profile of over 180 degrees, the light profile will be collimated to spread over approximately 120 degrees.

In another example, the alpha angle is between 0 degree to 7 degrees. This range may be used when there is no cladding on the outside of the light guide, the light guide is made of polycarbonate, and the light source is an LED. This range of alpha angle allows collimation of the light profile from 180 degrees to 90 degrees. If the light guide is made of another material, the alpha angle range may be reduced to between 0 degree and 5.5 degrees. For example, the other material may be PMMA.

In another example, the alpha angle is between 0 degree to 10 degrees. This range may be used when there is cladding on the outside of the light guide, the light guide is made of polycarbonate, and the light source is an LED. An alpha angle that is closer to 10 degrees will increase the amount of light rays that are kept inside the light guide.

In another example, the alpha angle is between 10 degrees and 20 degrees. This range allows all light rays to be kept inside the light guide.

In one example, the beta angle is between 0 degree and 7 degrees. This range may be used when the alpha angle is between 0 degree and 10 degrees. In this case, the exiting light profile is more collimated than the incoming light profile. A beta angle being approximately 3 degrees less than the alpha angle may result in a collimation effect to change the light profile from 180 degrees to 120 degrees. Thus, when the incoming beam is wider than the desired beam, the alpha angle is greater than the beta angle, and when the incoming beam is narrower than the desired beam, the beta angle is greater than the alpha angle, which may be zero.

In another example, the beta angle is between 7 degrees and 11 degrees. This range allows for a spreading of the light profile from a light source that may be too narrow, if there is no alpha angle. In one aspect of this example, the light source may be a light fiber with a numerical aperture (NA) value of 0.5 and the incoming light profile may be 60 degrees. In this case, the beta angle of between 7 degrees and 11 degrees will increase the exiting light profile from 120 degrees to 180 degrees.

Other values and combinations of the aforesaid alpha and beta angle ranges may be used as appropriate.

What is claimed is:

1. A vision device comprising:
an insertion tube;
an articulated bending section connected to the insertion tube, the articulated bending section including segments including a distal end segment; and
a tip part affixed to, and extending distally from, the distal end segment of the articulated bending section, the tip part including:
an electronic vision receptor;
a lens assembly positioned distally of, and longitudinally aligned with, the electronic vision receptor;
a light source comprising a light emitting diode;
a housing accommodating the electronic vision receptor and the lens assembly, the housing comprising a proximal housing part and a distal housing part arranged distally of the proximal housing part, the distal housing part having a window made of a first material that is transparent, the window having a proximal surface and a distal surface opposite the proximal surface, the window comprising a viewing part positioned distally of, and aligned with, the lens assembly, and the distal surface comprising a light emission surface disposed laterally of the viewing part; and
a light guide molded from the first material in one-piece with the distal housing part, positioned within the housing and extending proximally from the proximal surface of the window, the light guide having a predetermined length in a longitudinal direction between a light reception end and a light emission end of the light guide, the light source abutting the light reception end of the light guide, the light reception end configured to receive light emanated from the light source and the light emission end connecting the light guide to the proximal surface of the window and configured to emit the light,
wherein the light guide comprises, along at least a portion of the predetermined length, an expanding sector having cross-sectional areas, perpendicular to a longitudinal axis of the light guide, that increase in the longitudinal direction from the light reception end toward the light emission end, and wherein the cross-sectional areas have, along at least a part of the predetermined length, the shape of a rounded rectangle.

2. The vision device of claim 1, wherein the cross-sectional areas include a proximal cross-sectional area, wherein the expanding sector comprises a proximal surface perpendicular to the longitudinal axis and having the proximal cross-sectional area, and wherein the proximal cross-sectional area is smaller than any other of the cross-sectional areas of the expanding sector.

3. The vision device of claim 1, wherein the cross-sectional areas include a proximal cross-sectional area and a distal cross-sectional area, wherein the proximal cross-sectional area is smaller than any other of the cross-sectional areas of the expanding sector, wherein the distal cross-sectional area is larger than any other of the cross-sectional areas of the expanding sector, and wherein the expanding sector includes a lateral surface extending from the proximal cross-sectional area to the distal cross-sectional area at an alpha angle, from the longitudinal axis, ranging between 1 to 20 degrees.

4. The vision device of claim 1, wherein the expanding sector is shaped as a truncated pyramid.

5. The vision device of claim 1, wherein the expanding sector comprises a polymeric material and the expanding sector is geometrically configured such that at least 95% of the light received at the light reception end is reflected and at most 5% of the light is refracted.

6. The vision device of claim 1, wherein the cross-sectional areas increase in size in a continuous manner.

7. The vision device of claim 6, wherein the cross-sectional areas increase in a monotonous manner.

8. The vision device of claim 1, wherein the light guide further comprises, along at least a portion of the predetermined length distal of the expanding sector, a narrowing sector having cross-sectional areas, perpendicular to the longitudinal axis of the light guide, that decrease in size in the longitudinal direction from the light reception end toward the light emission end.

9. The vision device of claim 8, wherein the cross-sectional areas of the narrowing sector comprise a proximal cross-sectional area and a distal cross-sectional area, wherein the proximal cross-sectional area is larger than any other of the cross-sectional areas of the narrowing sector, and wherein the distal cross-sectional area that is smaller than any other of the cross-sectional areas of the narrowing sector.

10. The vision device of claim 9, wherein the narrowing sector comprises a lateral surface extending from the proximal cross-sectional area to the distal cross-sectional area at a beta angle, from the longitudinal axis, smaller than 14 degrees.

11. The vision device of claim 8, wherein the cross-sectional areas of the narrowing sector decrease in size in a continuous manner.

12. The vision device of claim 11, wherein the cross-sectional areas of the narrowing sector decrease in a monotonous manner.

13. The vision device of claim 1, wherein the expanding sector is configured to have a total internal reflection characteristic.

14. The vision device of claim 1, wherein the light guide comprises, along the predetermined length, a narrowing sector having cross-sectional areas that decrease in size in the longitudinal direction from the light reception end toward the light emission end.

15. The vision device of claim 14, wherein the narrowing sector comprises a truncated pyramid.

16. The vision device of claim 1, wherein the expanding sector of the light guide comprises a surface extending at an alpha angle to the longitudinal axis, the alpha angle being between 0 and 7 degrees.

17. The vision device of claim 1, wherein the reception end of the light guide comprises a blind hole, the light emitting diode positioned at least partly in the blind hole.

18. The vision device of claim 1, the tip part further comprising a support member having a proximal end and a distal end, the distal end positioned in the housing and the proximal end extending proximally from the housing and positioned in the distal end segment of the articulated bending section, the proximal end of the support member comprising a plurality of circumferential slots.

19. The vision device of claim 18, wherein the distal end of the support member comprises a portion extending between the light emitting diode and the housing and a portion ending proximally of the light emitting diode.

20. The vision device of claim 19, wherein the expanding sector of the light guide comprises a surface extending at an alpha angle to the longitudinal axis, the alpha angle being between 0 and 7 degrees.

* * * * *